United States Patent [19]

Cazaux

[11] 4,218,617
[45] Aug. 19, 1980

[54] MICRO-ANALYSIS PROCESSES USING X-RAYS

[75] Inventor: Jacques Cazaux, Reims, France

[73] Assignee: Agence Nationale de Valorisation de la Recherche (ANVAR), Neuilly sur Seine, France

[21] Appl. No.: 964,031

[22] Filed: Nov. 27, 1978

[30] Foreign Application Priority Data

Nov. 29, 1977 [FR] France .................................. 77 35901

[51] Int. Cl.² ............................................. H01J 39/00
[52] U.S. Cl. .................................... 250/305; 250/397
[58] Field of Search ........... 250/305, 306, 310, 396 R, 250/397, 398, 399; 313/359, 103 R

[56] References Cited

U.S. PATENT DOCUMENTS

| | | | |
|---|---|---|---|
| 3,760,180 | 9/1973 | Weber | 250/305 |
| 3,783,280 | 1/1974 | Watson | 250/305 |
| 3,866,044 | 2/1975 | Grund | 250/397 |

*Primary Examiner*—Bruce C. Anderson
*Attorney, Agent, or Firm*—Finnegan, Henderson, Farabow, Garrett & Dunner

[57] ABSTRACT

A process and device for micro-analysis in which a thin layer of anticathode material is scanned by means of a pencil-beam of electrons. The X-rays formed are received by a thin layer of converter where they give rise to a current of photoelectrons which is subject to an intensity measurement by an analyser.

From the measurement of intensity of the photoelectrons are deduced the properties of the zone of the anticathode which receives the pencil-beam.

17 Claims, 4 Drawing Figures

MICRO-ANALYSIS PROCESSES USING X-RAYS

BACKGROUND AND SUMMARY OF THE INVENTION

The present invention relates to micro-analysis using X rays.

Numerous processes of sample analysis are known in which the sample is scanned by means of an electromagnetic or corpuscular radiation probe and the secondary radiation is detected. The complete analysis of a material requires in general several analyses of this material to be carried out by different processes, such as ESCA, AUGER, X-emission, X-absorption, X-fluorescence, etc. Several specimens are prepared from the same sample and, at the present time, it is necessary to use processes carried out in different apparatuses.

The present day processes involving analysis of a beam of X-rays have well known disadvantages: the count rates are low, the sensitivity when trying to detect the light elements is low (since the proportional counters, generally used as detectors, have a window which absorbs the soft X-rays) and the energy resolution of the X-photons is still higher than 5 eV in the best case.

Furthermore, conventional spectrometry of the X-photoelectrons (ESCA) does not allow exploration by scanning, for the area of the sample illuminated by the X-rays cannot be reduced below approximately 1 cm². The area analysed in ESCA can however be reduced to a few μm², which allows exploration by scanning the sample to be analysed directly under the anticathode (J. Cazaux, Revue de Physique Appliquée, 10 (1975) p. 263). But this process is applicable only to the analysis of the sample in which the photoelectrons are created.

It is an object of the present invention to provide an improved process of micro-analysis using X-rays, answering better than those known heretofore the demands of practice.

If is a more precise object to provide a process which may be carried out in existing apparatus designed for implementing the ESCA or AUGER process.

According to an aspect of the invention, there is provided a process comprising the steps of forming an anticathode consisting of a thin layer of a material, scanning said anticathode with a thin beam of primary electrons to form X-rays, receiving said X-rays in a thin layer of a converter substance selected to have a photoelectronic spectrum which is simple and to exhibit one peak having a low bonding energy, collecting the current of photoelectrons resulting from absorption of said X-rays in the converter, measuring the instantaneous value of said current and determining the properties of the successive zones of the anticathode which receive the beam or the properties of zones of an absorbent layer placed between the anticathode and the converter.

To carry out a micro-analysis of the anticathode layer, the photoelectron beam is analysed by energy spectrometry and the distribution of a predetermined element in the anticathode is deduced from the intensity of a current of photoelectrons having an energy characteristic of this element. The energy resolution may be better than 1 eV and consequently makes it possible to determine the degree of oxidation of the element due to the chemical shift.

To measure the local absorption of an absorbent layer of a sample, placed between the anticathode and the converter, the photoelectrons may be collected, particularly when the sample is homogeneous, without discrimination in energy. A discrimination may be effected so that it measures the current of elastic photoelectrons due either to the radiation characteristic of the anticathode, or (at least in certain cases) to the fluorescence radiation emitted by the object. In both cases, a resolution of 10 eV is sufficient. If it is desired to analyse organic absorbent layers, an anticathode made from aluminum or magnesium will be advantageously used. In metallurgy, chromium will be used in preference. If the absorbent layer is formed by a light element, it will often be advantageous to form the anticathode from the element which follows the one forming the absorbent layer in the Mendeleen classification.

According to another aspect of the invention, there is provided a target for implementing the process defined above, comprising, forming a layer of a sample to be studied between a thick layer of a material forming the anticathode and a thin layer of a converter material. The sample may be organic (which will then lead frequently to sealing the edges of the anticathode and of the converter to form a sealed capsule protecting the sample) metallurgical or mineralogical. The material constituting the anticathode will be chosen with due consideration of the nature of the absorbent layer or that of the element to be detected therein.

The invention will be better understood from the following description of processes which form embodiments thereof given by way of examples. The description refers to the accompanying drawings.

SHORT DESCRIPTION OF THE DRAWINGS

DETAILED DESCRIPTION OF PARTICULAR EMBODIMENTS

In a first embodiment of the invention, the process is used for micro-analysis of a sample forming the anticathode by identification of its characteristic X-rays. For that, the kinetic energy $E_K$ of the collected photoelectrons coming from a converter layer is measured. The energy $h\nu$ of the X-rays of the kinetic energy $E_K$ and of the bonding energy $E_B$ of the material forming the anticathode are then determined by the relation:

$$h\nu = E_B + E_K$$

By adjusting the window of an analyser to kinetic energy $E_K$ corresponding to the energy $h\nu$ of the X-ray due to excitation of a predetermined element, the distribution of the X-emission of that element within the anticathode can be determined.

Figure 1:
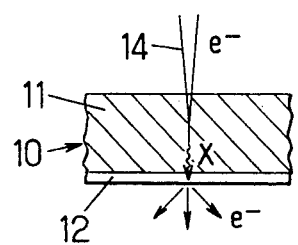
FIG. 1 is a simplified diagram showing a target, whose anticathode is formed by a layer of a sample to be studied.

Referring to FIG. 1, the anticathode layer and the converter layer are combined together in a composite target. The target 10 comprises an anticathode 11, formed by a layer of the sample to be analysed, coated with a layer 12, of small and accurately determined thickness, of a converter material of known nature, formed by a pure element or compound selected with respect to the element or elements to be detected in the sample material forming the anticathode, in accordance with criteria which will be given further on.

Figure 2:
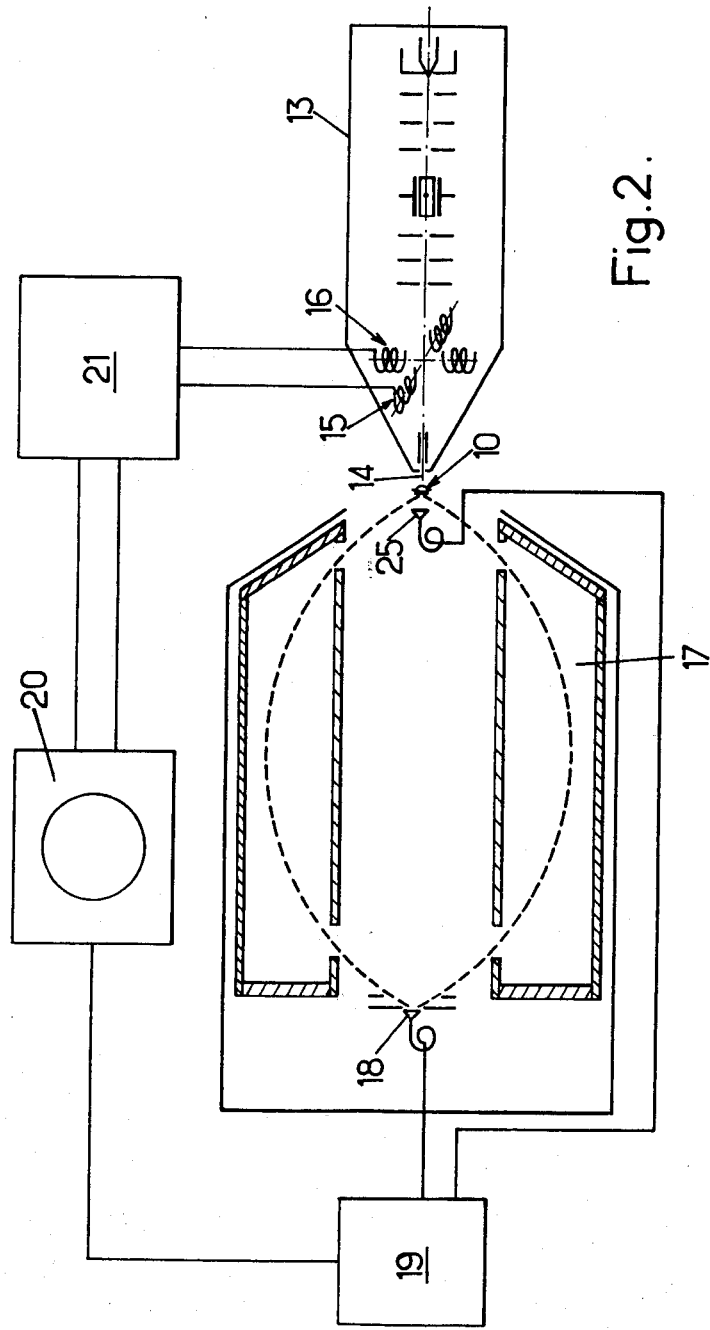
FIG. 2 is a simplified diagram showing the principal elements of an apparatus for carrying out the process.

The process may be carried out in an apparatus whose general construction is that of an AUGER microscope. Referring to FIG. 2, there is shown schematically an apparatus which comprises an electron gun 13 equipped with an optical system providing a fine pencil-beam of primary electrons 14 forming an electron probe, focused on target 10. By using an appropriate optical system, a definition of the order of a micron can be achieved.

The electron pencil-beam 14 is subjected to the action of a scanning device, shown schematically by two pairs 15 and 16 of deflector coils placed in two perpendicular directions. Conventional TV type scanning of target 10, can be achieved.

An analyser 17, for example of the cylindrical mirror type, which will not be described since it is of a type well known in the art, collects the photoelectrons coming from the converter material 12. It has a resolution of the order of 0.1 eV in the range from 100 to 500 eV.

The current measuring means 18 of the analyser is connected to electron amplification device 19 whose output drives a display unit 20, for example a cathode ray tube. Unit 20 is equipped with a scanning control circuit 21 which ensures synchronism between the scanning of the composite target 10 by the primary electron pencil-beam 14 and that of the display member.

The primary electron pencil-beam creates X-rays in the layer 11 which are characteristic of the elements which it contains. The X-rays are emitted in all directions. Some of the X-rays pass through layer 11 and reach layer 12 of converter material where they give rise to photoelectrons. The photoelectrons which escape from layer 12 in as large a solid angle as possible, are collected by analyser 17 which energy-analyses them and may, for example, be set to correspond to a characteristic X-line of an element to be detected.

The thickness of the layer forming the anticathode will be selected in dependance on the energy of the primary electrons. The maximum acceleration voltage of the electrons will typically not exceed 20 kV for reasons of convenience, space requirements for the gun and, price. In most cases, the voltage will even be limited to 10 kV, which makes the apparatus also suitable for carrying out analyses in AUGER spectrometry and in ESCA (electron spectrography chemical analysis). Under these circumstances, the anticathode will be used which has a thickness not exceeding 10 microns. On the other hand, since it is desirable for the primary electrons to be absorbed practically completely by the anticathode layer, the thickness will in general be at least 0.5 micron.

The converter will in general be formed by a pure element in having a good quantum efficiency and a spectrum as simple as possible and compatible with the nature of the elements to be detected in the anticathode. Whenever it is desired to detect light elements, the element forming the converter must have a low bonding energy $E_B$.

In particular, gold can be used which has the advantage of a high quantum efficiency. The intense double peak of gold is used corresponding to bonding energies $E_B$ of 83 eV and of 87 eV. Gold has different advantages: it is a good conductor of heat and it is easily deposited in the form of a fine layer of uniform thickness; it allows all elements to be detected, except lithium, helium and hydrogen.

However, when it is desired to avoid confusion between several photoelectronic lines excited by X-rays of different energies, while still keeping the possibility of detecting light elements, of low atomic number, amorphous carbon or boron may be used. The disadvantage of using a carbon layer as converter resides in the impossibility of detecting the carbon itself (frequent in organic samples), as well as the lighter elements, particularly boron, beryllium and lithium.

Again, in certain cases, compounds may be used for forming the converter layer. In particular, the use of lithium fluoride allows very light elements to be detected, the bonding energy of the lithium being very low.

The effective or useful thickness of the converter layer corresponds to the escape depth of the photoelectrons; consequently a very small thickness, not exceeding 0.5 micron, which is easy to obtain by evaporation when the material forming the layer lends itself thereto, will frequently be used.

The relative energy resolution $\Delta E/E$ of the electron spectrometer may easily reach $10^{-4}$. Consequently, the lines $k\alpha$ may be detected for the elements as far as zinc, and lines L or M for heavier elements, with an absolute energy resolution $\Delta E$ going down as far as 0.1 eV.

In another embodiment of the invention, there is placed, between the anticathode (formed by a pure chemical element or a chemical compound) and the converter layer, of small and even thickness, also formed from a pure material of known nature, a layer of the sample to be studied. The value of the photoelectron current emitted by the converter will depend on the absorption by the sample of X-rays emitted by the anticathode.

The measurement effected on the photoelectron current will be different for different types of analysis. A first approach is to collect all photoelectrons whatever their energy; this will be the case when, for example, it is desired to determine the variations of thickness of an homogeneous layer of the sample.

In another approach, energy analysis is used with an analyser adjusted either to detect the elastic photoelectrons excited by the X-rays emerging from the anticathode and having passed through the sample, or for detecting the photoelectrons excited by the fluorescence X-radiation emitted by the sample.

Figure 3:
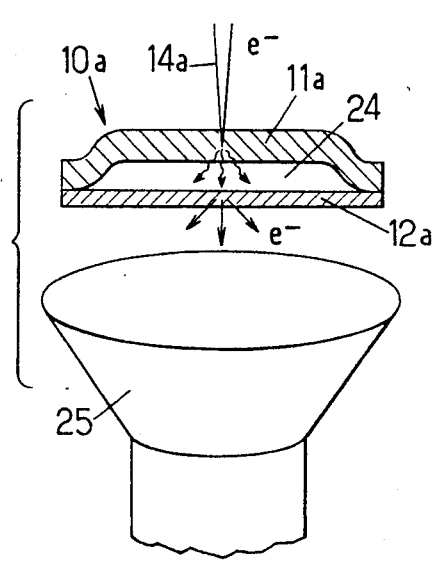
FIG. 3 shows schematically, in cross-section, a target according to another embodiment of the invention.

In all cases, a composite target will in general be used having the general construction shown in FIG. 3 (in which the elements corresponding to those of FIG. 1 bear the same reference number to which an a is added).

The composite target 10a comprises an anticathode layer 11a, which will in general be formed by an element in the pure state, in general a metal which has the advantage of high thermal conductivity. Since the acceleration voltage of the primary electrons forming the scanning pencil-beam 14a does not, in general, exceed 10 Kv, the radiations K of light and intermediate elements (up to zinc whose atomic number is 30) will in general be used and radiation L or M of the heavy elements. This is also true for the first embodiment.

However, when the sample to be studied contains light elements, such as carbon, nitrogen and oxygen, the principal constituents of biological samples, it is advantageous, to increase the absorption contrast, by using soft X-rays and, for that, to provide an aluminum or magnesium anticathode of which the Kα-radiation is excited.

On the other hand, in metallurgy or mineralogy, it will be advantageous to use radiation Kα of chromium. The thickness of the anticathode layer 11a will be of the same order as in the case of the embodiment of FIG. 1.

Figure 4:
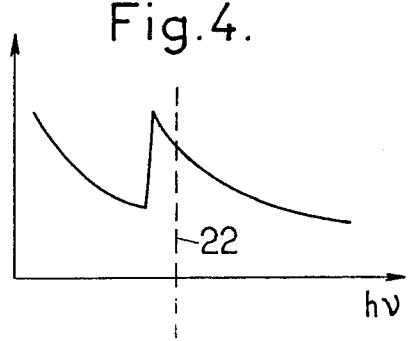
FIG. 4 is a curve representing the absorption with respect to the energy, bringing out the advantage of an appropriate selection of the energy window discrimination.

A sample to be studied can obviously be fractioned into several specimens, which are covered (for example by vaporization) with different anticathode layers, to obtain different contrasts from a given element and even to achieve inversion of contrast. To obtain maximum contrast, it will be advantageous to use an anticathode 11a which gives rise to X-rays with wavelengths slightly less than the absorption threshold of the element to be identified in the sample. In fact, as shown in FIG. 4, the absorption (shown on the Y-axis) for a given element will be much higher if X-rays are adopted with energy slightly greater than the threshold, as shown at 22 in FIG. 4. The sample 24 will be in the form of a layer with a thickness dependent on the absorption coefficient of the layer. A thickness may be adopted such that the absorption $e^{\mu x}$ lies between $10^{-3}$ and 0.9, but in practice the thickness will furthermore lie between 0.3 and 30 microns.

Finally, the converter layer 12a may be of the same elements as in the case of FIG. 1. However, since the energy analysis of the photoelectrons (when it is used) does not require a very searching energy resolution (an absolute resolution $\Delta E$ of the order of 10 eV being sufficient when no attempt is made to determine the chemical shift), a thin layer of gold may almost always be used whose thickness will not exceed 0.5 μm.

When the absorption of the X-rays by a sample layer of a light element is to be determined it will be generally advantageous to have an anticathode formed by the element which follows, in the Mendeleen classification, that which is to be detected. For example, to detect aluminium and magnesium in a thin film, the anticathode may be a thick layer of silicon or aluminium respectively. The converter material may in both cases be amorphous carbon or gold.

The layers forming the anticathode and the converter may form a sealed capsule protecting the sample from the effects of the vacuum which prevails in the apparatus. That possibility may be of great advantage for studying living particles which, if they were subjected to vacuum, would be immediately killed by dehydration.

As indicated above, the second embodiment of the invention may be used for determining the distribution of the absorption of X rays by the sample. In this case, a collection electrode 25 which collects all the photoelectrons leaving the converter may be used rather than an energy analyser. The maximum photoelectron current is obtained for a given intensity of the primary electron current, which allows either faster measurement or narrower primary electron pencil-beam (providing a better definition but corresponding to a smaller current).

By way of example, it will be noted that an overall quantum efficiency of the order of $10^{-8}$ may be achieved in the absence of a sample, with an aluminium anticathode and a gold converter layer. With an energy selection comprising a window of 10 eV, and a field effect gun which supplies a high primary electron current, a resolution of about 0.5 micron may be achieved at the cost of a slow scanning speed for recording a bidirectional image. If all electrons coming from the converter are collected, the current measured is increased by a factor which may be about $10^3$ since a continuous background of secondary electrons and photoelectrons which have been subjected to non-elastic impacts in the sample and in the converter is added to the current corresponding to the photoelectronic lines. With a normal scanning speed, a resolution of 0.5 micron can be reached.

By way the example, of application of the process by absorption to non-destructive control of LSI circuits can be cited. Indeed, the thickness of the insulation in conventional structures of the metal-oxide-semiconductor or metal-insulation-metal type may be measured by using the metal or one of the metals as converter. For example, in the case of a MOS structure of the Au—SiO$_2$—Si type, the silicon may be used as anticathode and the gold as converter. The gaps in the SiO$_2$ layer and its defects of homogeneity may be located. The same process may be applied in the case of a MOS structure of the Al—SiO$_2$—Si type. The latter layer, in general some microns thick, will again from the anticathode.

When it is not desired to determine the variation of absorption of the X-rays by the sample layer in two mutually orthogonal directions, but rather the distribution of a given element in the layer, energy analysis will generally be used.

Energy analysis will typically be carried out by adjusting the analyser so that its energy window overlaps the spectrum of the elastic photoelectrons excited in the converter layer by the characteristic X-rays emitted by the anticathode. Obviously, only the photoelectrons created in the part of the converter layer which corresponds to the escape-thickness escape from the exit face. This window is determined by taking into account the fact that the kinetic energy $E_K$ of these photoelectrons is given, from the energy $h\nu_c$ of the X-rays emitted by the anticathode and from the bonding energy $E_B$ of the photoelectrons, by the relationship:

$$E_K = h\nu_c - E_B$$

In certain cases, however, the analyser may be adjusted so that the current measured is that of the photoelectrons excited by the fluorescence radiation emitted by the object and having energy $h\nu_f$. In this case, the kinetic energy of the photoelectrons is given by:

$$E_K = h^v{}_f - E_B$$

Thus, can be determined the distribution of a particular element in the layer, while effecting an energy selection which corresponds to the value $h\nu_f$ characteristic of this element. Such a process can, for example, be used to determine the distribution of elements of an average atomic number, such as chromium, in the sample. It must however be noted that the fluorescence radiation is obviously much less intense than the radiation from the anticathode, and that in consequence the currents will be smaller and the implementing of the process will be slower.

In all cases, the process may be implemented by using an apparatus which can also serve for other types of analysis. It will be understood that the process of the invention thus completes the other known processes and, to a certain extent, serves as a substitute therefor.

The process of the invention may be embodied in numerous ways and may be implemented in an apparatus especially designed for this purpose. The apparatus may comprise, instead of a cylindrical mirror analyser, or in addition thereto, a device for collecting the whole of the photoelectrons emitted, providing possibly an amplification (a pancake of micro-channels for example).

I claim:

1. A process of microanalysis using X-rays, comprising the steps of: forming an anticathode consisting of a thin layer of material to be analyzed, scanning said anticathode with a thin beam of primary electrons to form X-rays, receiving said X-rays in a thin layer of a converter substance to generate a current of photoelectrons from absorption of said X-rays in said convertor substance, said converter substance selected to have a photoelectronic spectrum which is simple and to exhibit one peak having a low bonding energy, collecting the current of photoelectrons, measuring the successive instantaneous values of said current and determining the properties of the successive zones of the anticathode which receive the beam from said values.

2. A process according to claim 1, wherein the primary electrons have an energy less than 20 keV, the anticathode has a thickness between 0.5 and 10 microns and the converter has a thickness less than 0.5 micron.

3. A process according to claim 1 wherein the photoelectrons are subjected to energy selection before measurement of the current value.

4. A process according to claim 1, wherein the converter substance is selected from the group consisting of carbon, boron, gold and lithium fluoride.

5. A process according to claim 1, wherein the value of the beam is displayed on display means in synchronism with the scanning.

6. A process according to claim 1 for micro-analysis of the material forming the anticathode, wherein the beam of photoelectrons is energy-analyzed by spectrometry and distribution of an element in the anticathode is deduced from the current of photoelectrons in an energy gate characteristic of said element.

7. A process according to claim 1, wherein said energy analysis is carried out with an absolute resolution better than 1 eV whereby the degree of oxidation of said element can be determined by the photoelectrons whose energy is characteristic of said element.

8. A process according to claim 1, wherein said layer to be analyzed has a thickness such that its absorption of X-rays, $e^{-\mu x}$, is between $10^{-3}$ and 0.9.

9. A process according to claim 8, for measuring the local absorption of X-rays by the absorbent layer, wherein the anticathode is formed from the element which follows that forming the absorbent layer in the Mendeleen classification and the photoelectrons are collected without energy discrimination.

10. A process according to claim 1, wherein the photo electrons are subjected to energy analysis with a resolution of about 10 eV.

11. A process according to claim 1, for the analysis of absorbent layers formed by biological tissues containing one at least of the elements, carbon, nitrogen and oxygen, wherein the anticathode is of aluminium or magnesium.

12. A process according to claim 11, wherein the absorbent layer is sealingly enclosed between the anticathode and the layer of converter.

13. A process according to claim 1, for metallurgical or mineralogical analysis, wherein the anticathode is made from chromium and the X-rays correspond to the K$\alpha$-peak of chromium.

14. A target for implementing the process according to claim 11, comprising an anticathode layer made from aluminium or magnesium of a thickness between 0.5 and 10 microns, a layer of the material to be analysed and a layer of converter having a thickness less than 0.5 micron.

15. A micro-analysis apparatus for carrying out the process according to any one of claims 1, 6 and 7 comprising an electron gun for scanning a target with a pencil-beam of electrons whose energy is less than 20 keV and means for measuring the current of photoelectrons supplied by the target suitable for alternate use for X-emission, X-absorption, X-fluorescence, AUGER and ESCA analysis.

16. A process of microanalysis of a sample using X-rays, comprising the steps of: forming an anticathode consisting of a thin layer of a material, scanning successive zones of said anticathode with a thin beam of primary electrons to form X-rays, receiving said X-rays through an absorbent layer of said sample in a thin layer of a converter substance to generate a current of photoelectrons from absorption of said X-rays in said convertor substance, said convertor substance selected to have a photoelectronic spectrum which is simple and to exhibit one peak having a low bonding energy, collecting the current of photoelectrons measuring the successive instantaneous values of said current, and determining the X-rays absorption of the successive zones of the absorbent layer confronting said beam from said measured values as said beam scans successive zones of said anticathode.

17. A process according to claim 2, wherein the photoelectrons are subjected to energy selection before measurement of current values.

* * * * *